United States Patent [19]
Stout et al.

[11] Patent Number: 5,147,611
[45] Date of Patent: Sep. 15, 1992

[54] OPTICAL AND PYROLYZATE ANALYZER APPARATUS

[75] Inventors: Scott A. Stout, Fullerton; Rui Lin, Corona; Gunnar W. Recht, La Habra, all of Calif.; Joseph T. Senftle, Plano, Tex.; Stephen R. Larter, Venice, Calif.

[73] Assignee: Union Oil Company of California, Los Angeles, Calif.

[21] Appl. No.: 384,805

[22] Filed: Jul. 24, 1989

[51] Int. Cl.$^5$ .................... G01N 25/02; G01N 33/24
[52] U.S. Cl. ...................................... 422/78; 422/80; 422/82.05; 436/25; 436/31; 436/32; 436/155; 436/181
[58] Field of Search .................. 422/73, 78, 80, 82.05; 436/25, 31, 32, 155, 181

[56] References Cited

U.S. PATENT DOCUMENTS

| | | | |
|---|---|---|---|
| 3,588,440 | 6/1971 | Morse | 219/121 |
| 4,856,351 | 8/1989 | Smith et al. | 73/863.21 |

FOREIGN PATENT DOCUMENTS 0362577 12/1989 European Pat. Off.

OTHER PUBLICATIONS

"Laser Probe System for the Microscale Preparation of Carbonate and Sulfide Samples for Isotope Ratio Mass Spectrometry" by Arnold R. Taylor, 1985.
"Pyrolysis Methods, Pyrolysis Apparatus," pp. 68–71.
Interlase, Inc., "Instruction Manual Model 303," May, 1983.
Interlase, Inc. "Instruction Manual Model 303A Accessory Package," May, 1983.
"Application of Laser Microprobe (LAMMA 1000) to Fingerprinting of Coal Constituents in Bituminous Coal", Lyons et al, in International Journal of Coal Geology (1987), pp. 185–194, vol. 7, No. 2.
"Recent Development With the Laser Microprobe Mass Analyzer (LAMMA)", by Heinen & Holm, in Scanning Electron Microscopy/1984/vol. III, pp. 1129–1138.
"Solid State Mass Spectrometry Using a Laser Microprobe by Hercules", in Voorhees Analytical Hydrolysis, pp. 1–41, 1982.
"The Development of Laser Micro Pyrolysis of Coal Macerals", by Vastgla & McGahan, Americal Chemical Society, Fuel Division Preprint, 1986, vol. 31(1), pp. 53–56.
"Compositional and Structural Study of A Coal Surface Using a Laser Microprobe Mass Detector", by Dutta and Talmi, in Fuel, 1982, vol. 61, Dec., pp. 1241–1244.
"Using Laser Micro Mass Spectrometry with the Lamma-1000 Instrument for Monitoring Relative Elemental Concentrations in Vitrinite", By Morelli et al., Mikrochim. Acta 1988, vol. III, pp. 105–118.
"Application of the Laser Microprobe (LAMMA 1000) to the Microanalysis of Coal Constituents", By Lyons et al., New Frontiers in Stable Isotoyic Research, pp. 97–110.
"High Precision Spatially Resolved Analysis of $^{34}$S in Sulphides Using a Laser Extraction Technique", by Kelley and Fallick, Geochimica et Cosmochimica Acta, vol. 54, pp. 883–888, 1990.
J. Chromatoga, 56 (1971) 348–352, "Laser Pyrolysis of Oil Shales," by Biscar, pp. 348–352.
"High Energy (Neodymium) Laser Pyrolysis of Coal," by Vanderborgh et al., LA-UR-81-431, Submitted to Journal of Analytical and Applied Pyrolysis.
"Microscope-Laser Pyrolysis-Project Proposal," Jun. 1983, by Solli et al., Organic Geochemistry Dept., Continental Shelf Institute.
"Use of the Laser-Micropyrolysis-Mass Spectrometer in Studying the Pyrolysis of Coal," Symposium on Pyrolysis Reactions of Fossil Fuels presented before the Division of Petroleum Chemistry, Inc., American Chemical Society Pittsburgh Meeting, Mar. 23-26, 1966.

Primary Examiner—Jill A. Johnston
Attorney, Agent, or Firm—Gregory F. Wirzbicki; William O. Jacobson

[57] ABSTRACT

A heating and targeting laser beam and microscope apparatus optically senses, heats to generate a effluent fluid and chemically analyzes the thermal extract fluid or fluid pyrolyzates from a microscopic particle within a heterogeneous composite sample. A transparent duct-like chamber having a bottom opening is attached to a microscope. A contact surface of the sample is raised to abut against the bottom opening, which encloses the space around the particle and also brings the particle into the common focal plane of the microscope and the converging laser beam(s). This single step avoids the complex separate focusing and sealing steps required by present day techniques. The apparatus also includes an insulated and conductively heated collection probe and an inert gas supply (to efficiently sweep and collect the small amount of hot fluid and minimize condensation loss, secondary reactions, or complex heating devices), diverging-collimating-converging laser beam lenses (to achieve spot focusing as small as 10 microns) and a cold trap (to collect a series of fluid quantities). A collective analysis of the trapped fluid generated from a single type of particle is accomplished on a resolution quantity of fluid volatilized from the cold trap.

63 Claims, 3 Drawing Sheets

OPTICAL AND PYROLYZATE ANALYZER APPARATUS

FIELD OF THE INVENTION

This invention relates to the analysis by microscope and analysis by thermal extraction or pyrolysis of samples composed of microscopic particles. More specifically, the invention relates to devices and methods for the combined optical and thermal analysis of geological or other composite samples composed of different types of pyrolyzable microscopic particles.

BACKGROUND OF THE INVENTION

Many geological, biological, man-made and other solid materials are heterogeneous composite structures formed from interrelated, but microscopically and chemically discrete entities, such as particles or cells. If an analysis of the chemical or physical properties of this type of composite sample is desired, the analysis method and device must address these various microscopic entities. The primary objectives of an analysis of the properties of these composite samples are to: 1) locate and identify the physical structure of each type of particle within one sample; 2) identify the chemical or other properties of that particle type; 3) identify the physical relationships among the various particle types within the sample; and 4) be capable of analyzing a wide variety of particle types. The analyzer device should also be light weight, rugged in construction, low in cost, and easy to operate. The process using the analyzer should also be capable of several active analyzing and storage modes. These include: an on-line analysis mode, an off-line analysis mode, a temporary rest mode, and a long term storage mode. A minimum of effort to convert from one mode to another is also desirable.

Most of the current analyzers may accomplish some of these objectives well, but other objectives are accomplished poorly or not at all. A common analysis technique involves splitting the sample. A small sample portion is prepared for optical analysis (microscopic examination), while a second portion is prepared for a separate bulk chemical analysis, for example bulk analysis by pyrolysis. This two step process, however tends to be slow, complex, and unreliable. In addition, the bulk analysis step obscures the chemical properties of each particle as well as the relationships among the particles which comprise the composite sample, i.e., a sample composed of diverse particles. The bulk chemical analysis yields information from all particles producing significant pyrolyzates within the sample. It may not be possible to reconstruct the contribution(s) of each type of particle from the mixed particle pyrolyzate information generated by this bulk analysis approach.

The bulk analysis process step typically requires crushing, placing the crushed sample in an enclosed container, heating the crushed sample to elevated temperatures which generates a pyrolyzate fluid, and transporting the fluid to a chemical "bulk analysis" device. The enclosed container and heating device may also be part of the "bulk analysis" device. The chemical "bulk analysis" device may be a gas-liquid chromatograph, or a mass spectrometer or a nuclear resonance spectrometer. An example of devices used for this pyrolysis analysis method, without any means for optical viewing, can be found in U.S. Pat. No. 4,408,125.

This "bulk" method generates measurable quantities of pyrolyzates from groups of microscopic particles within a composite sample which individually could not generate sufficient pyrolyzates for chemical analysis. The bulk pyrolysis process can also be applied to large individual or groups of similar particles separated from the composite sample. However, physical or chemical separation of microscopic particles prior to pyrolysis is difficult, e.g., density gradient centrifugation. Furthermore, separation can alter the chemical and physical properties of the microscopic particles and destroy the relationships among these particles.

As an alternative to ordinary heating (pyrolysis or thermal extraction) sources, a laser beam can be used as a source of thermal energy or heating. This is illustrated in U.S. Pat. Nos. 4,025,790 and 4,672,169. The processes described in these patents are for gases, not particles. The laser selectively excites (i.e., the laser beam's infrared energy is absorbed by) certain gaseous compounds in a mixed sample within an enclosed chamber. Laser beam heating has several advantages. It allows for directing heat into a specific zone and rapidly heating (i.e., more quickly heating than conventional sources of heat) the specific gaseous compounds of interest.

The separate microscopic and thermal extraction or pyrolysis bulk analysis approach requires sample transport between the microscopic examination and the heating/pyrolyzate analyzer devices. The multi-step approach also tends to limit the speed and use of devices in this sequential step type of analysis. One can also never be sure that the spit sample portions are identical for composite samples. Reconstruction of each type of pyrolyzate producing particle present in the composite sample from the bulk information produced, even if possible, can also be unreliable.

An integrated optical and pyrolysis approach is also known. One integrated approach modifies a laser heating pyrolysis system by adding a microscope. The sample is placed in a pyrolysis chamber which includes a window for microscopic examination and laser beam transmission. In addition, other equipment may be required to allow optical focusing, illumination, and sample viewing placement, removal, and manipulation.

The optical modifications to the basic pyrolysis chamber design compromise the performance of both the optical and pyrolysis analysis systems. For example, the combined device must: 1) accommodate the transmission of the narrow laser beam and the microscope's broader light beam or field of view; 2) allow for the proper sample focusing of the laser beam and optical microscope systems; 3) allow sufficient space between the sample and the window to avoid window clouding and overheating from contact with the hot pyrolyzates, but be close enough to avoid changing the focal lengths of each system; and 4) provide a chamber large enough to include the added components but not so large as to dilute or ineffectually collect the small quantities of pyrolyzates which may be produced. In addition, the multiplicity of elements required to accomplish both analyses tends to get in the way of each other in the confined space of a pyrolysis chamber. This further limits operational use, reliability and flexibility. These problems also tend to limit the combined analysis device to specific sample sizes and particle types.

A second method, which is the inverse of this first integrated approach (modifying a pyrolysis system), converts an optical system (microscope). The optical system is modified to include a colinear heating laser beam and an open sided chamber. The open side of the chamber is placed on a conventional glass slide on the microscope stage. The remainder of the system includes a chamber window, a supply of a purge gas, and a collection tube. This second or inverse integrated approach is illustrated in U.S. Pat. No. 3,941,567. However, this inverse approach also requires design compromises similar to the first integrated approach.

A specific sample of the integrated approach design comprises and problems occurs if analysis of a single type of particle within a composite sample is desired. Focusing of the pyrolyzing laser beam requires a narrow beam, smaller than the representative dimension of the particle. The laser beam or particle location must also be adjustable, so that the beam may be pointed or aimed at the spot on the particle of interest. The adjustment may also require refocusing of both the microscope and laser systems. Very small individual particles may not be capable of generating sufficient pyrolyzate upon laser beam heating to be detected by an analyzer, even if the beam is narrow and properly focused. These problems may limit the application of this combined laser and microscope system to only larger particles within the composite sample.

The collection of the hot gaseous pyrolyzate fluids also presents problems. Hot pyrolyzate gases tend to condense on any cooler (i.e., ambient) temperature surfaces of the chamber. Heating the chamber may prevent condensation, but can lead to optical distortions, thermal expansion, seal failures, and outgassing of chamber materials, and pyrolysis of other particles (causing bulk release and contamination of the analysis).

SUMMARY OF THE INVENTION

A simple apparatus and method capable of determining properties of very small individual particles in composite samples is needed to overcome the limitations of the prior art. The method should also minimize complex sample preparation, sample inserting and positioning, chamber enclosing/sealing, separate focusing, heating errors, and post-pyrolysis reconstruction of multi-pyrolyzate bulk information.

These and other needs are met by a method of using an integrated laser heating and microscope apparatus including a shaped chamber attached to a microscope, the chamber having an opening at its lower side and a thermally insulated and conductively heated gaseous pyrolyzate collection tube. The chamber is transparent to visible and laser heating beam transmissions, and the insulated collection tube is conductively heated to prevent pyrolyzate condensation. A composite sample surface (containing one or more particles of interest on an exposed surface) serves to seal the chamber opening when it is raised toward the opening of the chamber. Raising the sample on the microscope stage both encloses the sample surface and brings the particle into the common focal plane of both the microscope and laser systems. Using incident light illumination, a small spot on the particle of interest is selected (by observation through the microscope) and centered within the field of vision.

A heating laser beam diameter is first expanded to be conveniently converged and focused directly onto the diffraction-limited spot on the particle of interest. The beam expansion and converging process and impact generates a small quantity of pyrolyzate gases from a single pre-selected particle spot. After the spot heating, the small quantity of effluent pyrolyzate gas is both sucked and swept (by an inert gas supply flow within the shaped chamber) into a conductively heated tube which carries the gases to a cold trap, where condensed hot pyrolyzate gases are retained. Additional heating bursts by the laser beam at different spots on the particle or other microscopically identical particles of the same type, generates added pyrolyzate gas quantities which are collectively stored in the cold trap. Collection and storage continue until a sufficient quantity for analysis is retained in the cold trap. Warming the cold trap vaporizes the stored multi-burst pyrolyzate gas quantities, which are then sequentially analyzed by a gas chromatograph and a mass spectrometer.

The multi-burst process, small spot focusing, collection tube placement and insulation, and transparent chamber shape allow quick optical and thermal extraction or pyrolysis analysis of a particle within a composite sample previously too small for combined analysis. The apparatus also permits both a microscopic and chemical analysis on the same exact particle and avoids previous design compromises and problems.

BRIEF DESCRIPTION OF THE DRAWINGS

Like numerals refer to like elements.

DESCRIPTION OF THE PREFERRED EMBODIMENT

Figure 1:
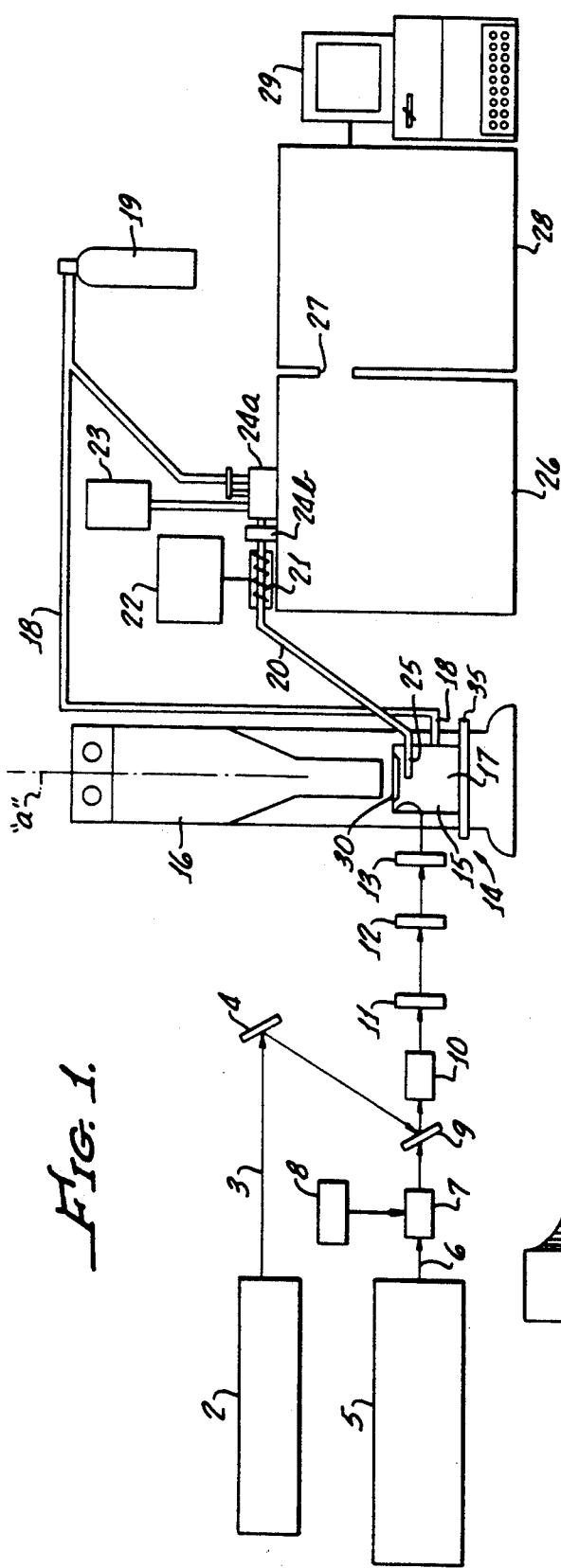
FIG. 1 shows a schematic of a combined microscope and pyrolysis analysis system.

FIG. 1 is a schematic representation of an optical and thermal extraction or pyrolysis analysis system for analyzing a particle within a composite sample. A first or optical laser source 2 provides a low power visible beam of light 3 to a fixed mirror 4. The diameter of beam 3 at the source is typically less than 2 mm. and is approximately 0.6 mm. in the preferred embodiment. The optical laser source 2 in the preferred embodiment is provided by a red Helium-Neon laser having a wavelength of 632.8 nanometers, but any laser device for generating a low intensity (typically less than 0.01 watt) beam of electromagnetic radiation within the visible spectrum is acceptable. The visible laser beam 3 targets a second near-infrared (and not visible) laser beam from heating energy source 5.

The second or near-infrared or heating laser beam source 5 produces an infrared or near-infrared laser beam 6 directed to an electronic shutter 7. The near-infrared laser source 5 in the preferred embodiment is provided by a 5 W continuous wave Nd:YAG laser, but any device for generating sufficient energy or heat can be used. The laser output is polarized and the laser source is operated in a multi-mode rather than a single mode to obtain full power capability. The laser source 5 must generate a laser beam of electromagnetic radiation within a frequency band which is a) absorbed by (i.e., heats) a particle within a composite sample 32 (see FIG. 2), and b) of sufficient intensity to generate a thermal extraction or pyrolyzate fluid. Laser frequencies are expected to be within the near-infrared, middle-infrared and far infrared bands, i.e., wavelength of between 0.75 to 1000 microns). In addition to the preferred near-infrared laser source 5, other embodiments may employ alternative or added sources of heat and absorbed energy, such as additional heating laser beams or contact filament heaters.

Whether the laser beam from infrared source 5 passes through shutter 7 is governed by shutter control device 8. Shutter control is preferably accomplished by a digital programmable function set to open the shutter for a selected time period ranging from 10 to 990,000 milliseconds. Selection of the shutter opening time can be based upon observed particle material, particle size, particle shape, and the amount of pyrolyzate desired. Shorter or longer digital or manual shutter control times are also possible in other embodiments. Shutter control 8 may also be a chopper, allowing a series of repeated pulses of the near-infrared laser beam 6 to be transmitted to the beam splitter 9.

The beam splitter 9 is a dichroic mirror. The dichroic mirror can coaxially combine the visible beam 3 reflected from fixed mirror 4 and transmit the near-infrared beam 6 to a variable attenuator 10. The attenuator 10 contains a prism and waveplate. These attenuate the polarized output of the Nd:YAG laser source 5 as the waveplate rotates in a plane perpendicular to the incoming beams. A polarized lens can also be used to attenuate the intensity of the laser beam. Attenuation control (not shown for clarity) can be by manual or device driven rotation of the attenuator 10. This selectably allows a full attenuation range from 0% to 100% of the near-infrared laser beam's energy to be transmitted to a diverging input lens 11. "Diverging" input lens 11 in the preferred embodiment is actually a converging lens in which the beam is converged to a focal spot after which the beam diverges. The converging lens 12 is placed at a divergent beam location, i.e., past the focal point.

In order to focus the near-infrared 6 and visible beams 3 onto a very small (approximately 10 micron diameter), diffraction limited spot on the composite sample 32 (see FIG. 2), conventional (2 mm. cross sectional beam diameter) laser beam sources must be even further reduced. Instead of directly converging the 2 mm. laser beam over the distance between converging lens 13 and the sample surface (requiring very small or specialized components), the beam diameter is first expanded in the diverging input lens 11 to more conventional dimensions, then collimating the expanded beam in a converging output lens 12 before finally converging the beam to a focal point or spot. A final converging achromatic lens 13 narrowly focuses the expanded and collimated beam(s) onto a spot within both the microscope's optical field of view and the focal zone in the sample chamber 14. This initial diverging-collimating converging lens arrangement allows the achromatic converging lens 13 to have a diameter ranging from 1.5 to 4.0 cm. Focal length of the converging lens 13 is between 70 and 80 mm. in the preferred embodiment to allow coincidence at the microscope focal plane (at the sample surface). Without this initial diverging and collimating lens arrangement, attaining a diffraction-limited point or spot size of 10 microns on the sample surface would not be possible.

The sample chamber assembly 14 includes a container 15 attached to the objective lens portion of an incident light microscope 16. The container 15 can have a variety of shapes and sizes, but all containers partially enclose a cavity 17 and have a bottom opening near the optical axis "a." Chamber shape and size allows accomplishing two objectives in a single step. Covering the bottom opening both seals the chamber and locates the sample surface (see FIG. 2) containing the particle of interest within the cavity 17 and at the microscope's focal plane or zone (zone of maximum sensitivity or focus). The focal zone is along the optical axis "a," around which an optical field of view of the sample can be detected by an observer. In other configurations, the microscope 16 may be any sensor of radiation emanating from a sample to be analyzed.

The container 15 shown in FIG. 1 includes a first optical window 30 and a second laser window 38 (see FIG. 2) to allow microscopic examination and the visible and near-infrared laser beams to enter the cavity 17 partially enclosed by the container 15. The microscope 16 includes a 50× (magnification power) long-working distance air objective lens located proximate to the sample chamber 14 and a 12.5× eye piece lens to provide 625×. However, the magnification power may be modified in other embodiments by replacement of the objective or eye piece lenses, if the focal length is consistent with the chamber and sample placement.

The microscope 16 can view a variety of particles on one surface of the composite sample. The viewer can identify a particle of interest on an exposed surface of the prepared sample located within the cavity 17 (see FIG. 2). The particle of interest in a sample surface is located near the optical axis (center of the field of view of detectable light) and within the focal plane or maximum sensitivity zone of the microscope 16. An adjustable mirror 39 (see FIG. 2) points the visible (red) laser beam 3 onto the spot on the particle of interest. The near-infrared laser beam 6, controlled by shutter 7, intensively and instantaneously heats and/or pyrolyzes a portion of the desired particle. The laser heating generates a plume of gaseous or liquid effluents (fluid pyrolyzates) into the cavity 17.

The specific container 15 shown in FIG. 1 also includes a port for transmission of a purge or inert gas piping 18 to the cavity 17 from a supply or source of inert gas 19. In the preferred embodiment, helium and a helium tank is the inert gas and the inert gas source 19, respectively, but other purge or inert gases and sources may be used. The helium gas purges the cavity of air and contaminating gases before pyrolysis and acts as an inert gas carrier for the small quantities of pyrolyzates generated from the small spot on the particle of interest by the near-infrared laser beam.

The container 15 also includes a port for a collection piping system 20. An electrical resistance heater 21 heats portions of the collection piping system external of the container 15 to a minimum temperature controlled by temperature controller 22. The minimum temperature of the piping system 20 must be sufficient to prevent the condensation (or other change of phase) of the hot pyrolyzate gases. Ceramic insulation 44 (see FIG. 4) thermally insulates the portion of the cavity protruding collection piping from the cooler (unheated) components of container 15. Ambient air natural convection cools the outside of container 15.

Alternative embodiments may allow for cooling the outside of container 15 (and associated components in thermal contact with the container) by forced convection or placement of the container 15 in a temperature controlled environment. Still other alternative embodiments may provide for heating or cooling the entire chamber, or insulate only a window or heat sensitive portions of the apparatus. These other alternative embodiments allow more extensive chamber heating or cooling, further minimizing condensation loss of pyrolyzate gas on cool chamber components.

The cavity protruding portion of the collection piping system 20 is heated by conduction to a minimum temperature which avoids condensation of the hot pyrolyzate gases. Because of thermal inefficiencies or insulation losses, the external piping portion is at a slightly higher temperature than the temperature of the cavity protruding portion of the piping system 20.

The collection piping system 20 can be used to first evacuate the cavity 17 by a vacuum pump 23 prior to or in place of inert gas purging. After purging, the vacuum pump 23 can remove excess purge gas from inert gas piping 18. After heating and pyrolysis of a portion of the microscopic particle enclosed by container 15, the collection piping 20 collects the effluent pyrolyzate gases for analysis. Control of vacuum, purge and gas collection is accomplished by a manual valve 24a and a cold trap 24b. Manual valve 24a in the preferred embodiment is a six way manually-actuated valve, but may be one or more solenoid valves controlled by an electronically programmed gas controller in other embodiments.

A source of liquid nitrogen (not shown for clarity) cools cold trap 24b to quickly condense and retain (trap) all the pyrolyzate gas while passing the inert (low condensation temperature) purge/carrier gas. The cold trap can be used to combine multiple quantities of pyrolyzate each time the shutter 7 and near-infrared laser 6 (see FIG. 1) produces thermally generated extracts or hot gaseous pyrolyzates. Each quantity of pyrolyzate or thermal extract gases emitted from each burst or shuttered exposure may not be sufficient to perform an analysis by an analyzer device, i.e, the quantity may be below the minimum resolution amount needed by an analysis device. After collecting a sufficient quantity of gases for analysis, the cold trap warms by isolating the coolant source and natural convection contact with the ambient air (and possible heating from the analyzer device), vaporizing and releasing the trapped pyrolyzates.

In alternative embodiments, one or more cold traps may be at other locations along the piping collection system 20. One cold trap may be placed close to the container 15, minimizing the length of tubing which must be heated during pyrolysis. In another embodiment, the cold trap could be placed adjacent to the chamber, cooling (by conduction) the collection piping portion protruding into the chamber. This alternative embodiment avoids the need to heat the collection piping system altogether. The conductively cooled protruding tube acts as part of the attached cold trap, condensing the pyrolyzate as it emanates from the sample surface. Multiple trapped pyrolyzate quantities may again be later vaporized for mass spectrometric or other analysis. If the trap is transported while cold (at below pyrolyzate condensation temperatures), analysis can be accomplished off-line at a different location.

The protruding and insulated collection piping portion 25 (see FIGS. 1 and 4) of the collection piping system within cavity 17 has one end located proximate to the sample surface containing the particle of interest (i.e., the particle to be analyzed). The shape and dimensions of inert gas supply piping 18 and the protruding portion 25 tend to suck and sweep gases from the pyrolyzate plume and face of the sample near the particle of interest. The protruding portion can also be deformably adjusted to optimize pyrolyzate sweep efficiency at different points of the sample surface. Alternative embodiments would include multi-port or multi-position protruding tubes as well as variously shaped nozzles and tubes.

Analysis of the pyrolyzate collected in the collection piping system 20 may be on-line (real time analysis with a warm cold trap 24b) or off-line (gas collected in cold trap 24b, and analyzed at a later time). The control valve 24a can divert the collected pyrolyzate directly (on-line mode) to a first chemical analysis device 26. In the preferred embodiment, the first pyrolyzate analysis device is a gas chromatograph, but other chemical analysis devices or methods can also be used. The increasing temperature in the internal heat source or oven of the gas chromatogragh heats and volatilizes a stream of the "lighter" (i.e., low boiling point) gas components of the trapped pyrolyzate gases. "Heavier" (i.e, higher boiling point generally having higher molecular weight) components are then produced as the temperature increases. The individual components of the pyrolyzate (and inert carrier) gas stream are chromatographically separated and are then transferred by a transfer section 27, to a second pyrolyzate chemical analysis device 28. The gas chromatograph and transfer section 27 must also be heated to avoid pyrolyzate condensation. The second chemical pyrolyzate fluid analysis device 28 in the preferred embodiment is a mass selective detector or mass spectrometer, but other chemical or other property detection and analysis devices can also be used. Data system 29 collects and stores data from one or both pyrolyzate analysis devices for display, evaluation, and analysis.

Optical window 30 transmits visible frequency electromagnetic radiation (light) from the sample within cavity 17. The emitted light from the particle is seen by a viewer observing the sample through microscope 16. The microscope field of view at the focal plane encompasses more than one particle within the sample in order to select the microscopic particle of interest 49 (see FIG. 7).

Figure 2:
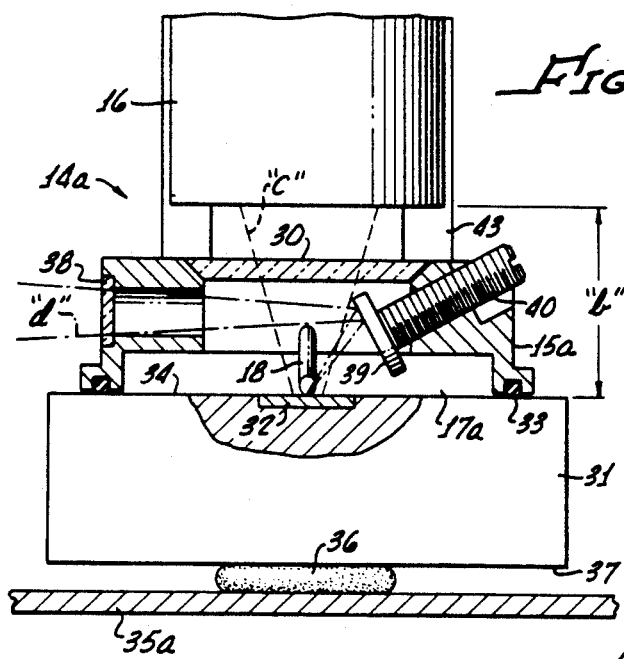
FIG. 2 shows a front schematic cross sectional view of a first alternative sample chamber portion of the analysis system.

FIG. 2 is a front schematic cross sectional view of a first alternative embodiment of a sample chamber 14a. The open side of container 15a is sealed in a fluid tight arrangement against the polished surface of an encasement 31 of sample 32. The shape and dimensions of container 15a again place a polished surface 34 of the sample 32 and sample encasement 31 at the focal plane of microscope 16 when container 15a abuts against the polished surface 34. The encasement 31 of the sample 32 is composed of a cast-in-place, transparent acrylic plastic. Grinding one of the surfaces 34 of sample 32 exposes and polishes a planar surface.

Other encasement or potting materials can also be used in other embodiments to support and orient the sample from the microscope stage 35 (see FIG. 1) and-/or glass slide 35a (see FIG. 2). The sample 32 can also be cut or sliced from a larger sample before casting or encasing within the plastic to form the encased sample. Normal microscope illumination (either from above or below the sample) is sufficient without any added illumination when the encasing material is translucent.

The polished surface 34 of the encased sample 31 provides a sealing surface for an end seal 33. The end seal 33 is an O-ring attached to the container 15. The O-ring generally defines the container opening or aperture. In the embodiment shown, the O-ring is composed of neoprene. Different shapes or O-rings composed of Teflon, Viton or other elastomeric compounds may also be used.

The apertured container 15a is attached to the microscope 16 (shown in part in FIG. 2) while the glass slide positions the attached spaced-apart particle in sample 32. The glass slide 35a is supported by the microscope stage 35 (see FIG. 1). The sample stage can be raised or lowered to bring the polished sealing surface 34 of the encased sample 31 into focus, as observed through the microscope 16. Height or distance "b" is selected to be approximately equal to the focal length of the objective lens located in the lens barrel of the microscope 16 near the sample 32. The height or distance "b" from the sample surface 34 (including the particle of interest) to the lens barrel is 1.25 cm for the lens configuration described.

Adjustment of the microscope focus moves the microscope's sample platform or microscope stage 35 along direction "a" (see FIG. 1). Adjustment is capable of abutting the end seal 33 against the polished sample and plastic surface 34 to effect an enclosure and sealing of cavity 17. One movement (up and down direction "a") of the stage 35 is typically accomplished by a knurled focus adjustment knob and mechanism (not shown for clarity) of the microscope 16. After end seal 33 abutably contacts the sealing surface to form a generally sealed cavity 17a, the sealed cavity can be purged of ambient air with helium, evacuated or pressurized. Chamber 15a is attached to the lens barrel of microscope 16 by an attach member 43 (see FIG. 4).

Optically viewing the sample through the microscope 16 (shown as dashed lines "c" on FIG. 2 emanating from a field of view on the polished surface of sample 32 and reaching the microscope 16) is accomplished through optical window 30. The field of view in the focal plane on surface 34 of the sample 32 encompasses many microscopic particles. The microscope observer selects one spot or portion of a single particle for near-infrared laser beam pyrolysis. In the embodiment shown, the optical window 30 is composed of BK7 quartz glass, having a diameter of approximately 1.5 cm and a thickness of approximately 0.25 cm. These window dimensions and material provides maximum visibility and structural strength to withstand the vacuum or pressure within the cavity 17a. The light source (not shown for clarity) for illuminating the field of view may be a variety of sources currently available for microscope illumination.

The source of light may be placed above the cavity 17 illuminating through the window 30 and emitted back (reflected) as light from the polished surface 34. The source of the light may also be placed below the sample 32, transmitting light through a transparent encasing or potting plastic and thin (translucent) sample 32. In other embodiments, a source of light may be placed within the cavity 17a, if required. Proximate to the truncated cone of light "c" from the field of view of the microscope 16 is one end of the purge gas piping 18.

The encased sample 31 is adjustably mounted in putt 36 directly on the microscope sample stage 35 (see FIG. 1), or glass slide 35a supported by sample stage 35. Putty-like or clay material 36 is placed between the bottom surface 37 of the encased sample 31 and the microscope sample stage 35 or glass slide 35a. Compressing the clay 36 between the encased sample 31 and glass slide 35a forms an adjustable and removable position support and attachment. The direction and amount of pressing place and orient the polished surface 34. This location provides for optimum viewing and pyrolysis within the focal plane of the microscope 16 and at the small focal spot formed by the converging laser beam(s).

The pressing of the clay 36 is done in a conventional hand press tool, having a stop fixture (not shown for clarity). The stop fixture surface orients the pressed surface to a height within the common microscope and laser beam focal planes/spots, and prevents further pressing of the sample onto the glass slide 35a. A set-off spacing ring surrounding the sample in the press can serve as the stop fixture (not shown). The spacing ring assures a set-off spacing and parallel alignment of surface 34 within the field of view of the microscope concurrent with chamber sealing.

Mounting of the sample on the glass slide 35a also allows lateral motion of the particle within the focal plane. This is accomplished by lateral motion of the glass slide 35a (and attached sample) on the parallel microscope stage below the glass slide 35a (see FIG. 1). This lateral motion can be accomplished by hand or by mechanical clips and adjustment means (not shown for clarity) commonly provided on microscope sample platforms or stages. Mechanical means of lateral motion adjustment allows precise placement under higher power magnification.

The laser beam (shown as dotted lines "d" in FIG. 2) emanating from either laser source (shown in FIG. 1) passes through the second or laser window 38. The laser window shown is composed of ZnSe, having a diameter of 0.6 cm and a thickness of 0.3 cm. This material and the dimensions maximize the amount of laser beam radiation transmitted and the ability to withstand the heat and expected vacuum or pressure cavity conditions. Alternative laser window materials of construction, such as sapphire, may also be used. The diameter of the laser window 30 is small compared to the optical window because the converging laser beam diameter is small. The converging beam diameter also minimizes the required size of the laser mirror 39. The entire chamber may also be made of a transparent material, eliminating the need for separate windows.

The adjustably mounted laser mirror 39 allow the user to direct the beam to the center of the field of view or to point the laser beam upon different spots on the selected particle within the sample 32 while maintaining the focus. The laser mirror 39 is preferably composed of glass, internally coated with silver, but may also be gold- or aluminum-coated glass or plastic. The adjustably mounted mirror is at approximately a 22.5 degree angle to the incident laser beam "d" and threadably moves the mirror along the inclined axis using threaded shaft 40. Alternative embodiments can include non-planar mirrors, alternative angles or a plurality of adjustable mirrors for flexible and precise location and direction of laser beam impingements on the selected spot.

The threaded shaft 40 has a slot at the exposed end of the threaded shaft to allow screwdriver adjustment of the laser mirror 39. If necessary, the shaft and mating threaded port in the container may include a rotating seal to better retain a vacuum or pressure in the cavity 17a. It should be noted that FIG. 2 is not drawn to scale to better illustrate the laser-related components which are generally smaller than shown.

Figure 3:
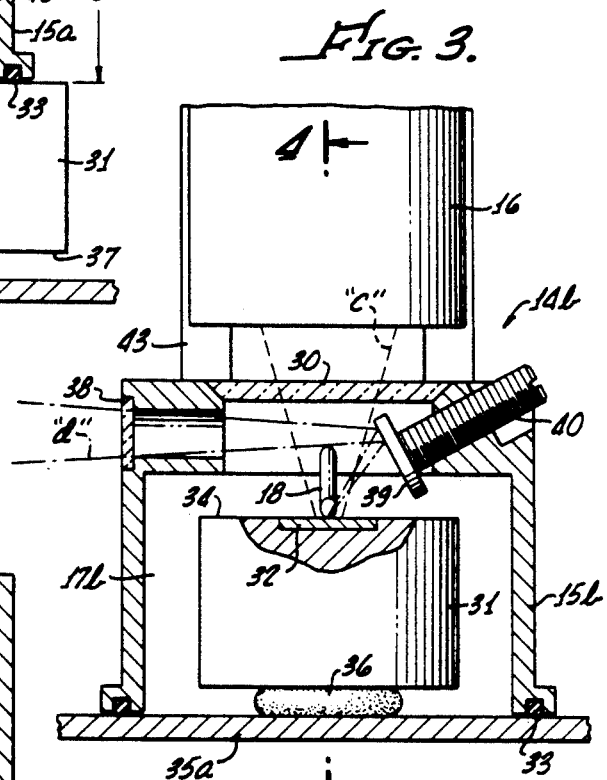
FIG. 3 shows a schematic front cross sectional view of a second alternative sample chamber.

FIG. 3 shows a schematic front cross sectional view of a second alternative embodiment of the sample chamber 14b. The open sided container 15b extends to the microscope glass slide 35a instead of the encased sample 31 as shown in FIG. 2. The encased sample 31 is again pressed against clay 36 in a fixtured press to obtain a repeatable height and orientation of the exposed surface 34 of sample 32. The location of the surface 34 is at the common focal height with respect to the microscope 16 and laser spot focusing systems when the chamber is nearly enclosed or forming a boundary for the effluent gases.

Through the microscope 16, the observer selects a particle of interest and identifies the relationships with adjoining particles. The observer then selects the spot on the particle of interest within the exposed surface of sample 32 to be analyzed by pyrolysis. Focusing the visible laser beam 3 (see FIG. 1 and narrowing lines "d" shown on FIG. 3) on the selected particle spot is accomplished by adjusting threaded shaft 40 and attached mirror 39 (or moving the particle to the center of the field of view) while observing through the optical window 30 and microscope 16. The near-infrared laser 6 (see FIG. 1) heats and pyrolyzes a 10 micron sized spot on the selected particle at the exposed surface. The observation, selection and spot pyrolysis is repeated at another portion of the same (or different) particle. Multiple laser heating bursts can be used to obtain a minimum resolution amount of pyrolyzates from the same particle, or the same type of particle, required by the chemical pyrolyzate analysis devices (see FIG. 1).

Figure 4:
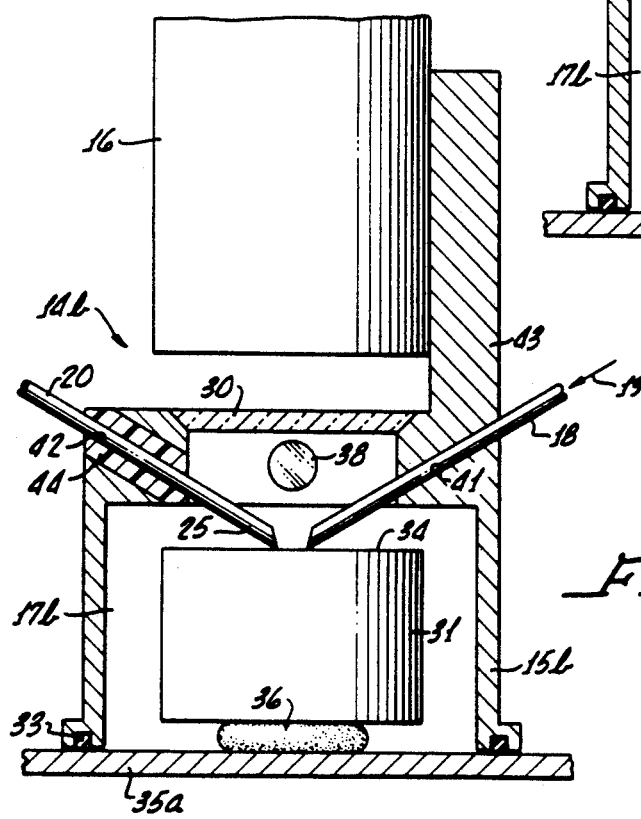
FIG. 4 shows a schematic side cross sectional view of the sample chamber shown in FIG. 3.

FIG. 4 shows a schematic side cross sectional view 4—4 of the second alternative sample chamber 14b shown in FIG. 3. The sample chamber 14b comprises the container 15b and attachment element 43. The attachment element 43 attaches container 15 to the objective lens barrel of microscope 16. The attachment element 43 places the sample chamber 14b so that focusing motion of the glass slide 35a also brings a sample surface into a common focus and sealed position.

The open ended container 15b has supply port 41 through which inert gas (from piping 18 and inert gas supply 19 shown in FIG. 1) is provided to the cavity 17b. The supply piping 19 shown in FIG. 2 extends to a point near the spot at the central portion of the cavity 17b to improve gas sweeping into the collection piping 20. Alternative construction would also comprise fittings attached to the container 15b and a flexible extension of the supply piping within the cavity.

The collection system piping 20 and the protruding piping portion 25 pass through a collection port 42. The collection port 42 includes a thermal insulation 44. The thermal insulation is composed of a ceramic material, but may be any other insulation material or structure capable of withstanding elevated temperatures needed to prevent condensation of pyrolyzate gases, approximately 290° C. in the embodiment shown in FIG. 4, and structurally capable of withstanding any expected pressure or vacuum within the cavity 17b. The insulated design of the collection port 42 and thermal contact between interior and exterior (to the container) portions of the collection piping, allow the resistance heater 21 (see FIG. 1) to heat the collection piping 20 including the protruding section (or chamber interior portion) 25 by conduction. The laser window 38 is centrally located on one side to point the laser beam onto the adjustable mirror, thereby reflecting the beam onto the exposed surface of the encased sample 31. The protruding portion 25 of the collection piping is also located proximate to the laser impingement spot on the encased sample 31. Although collection piping and the supply piping is shown in FIG. 4 extending to the front and rear, respectively, of the chamber, alternative embodiments can place the piping and ports in other locations, angles or orientations within the chamber.

Figure 5:
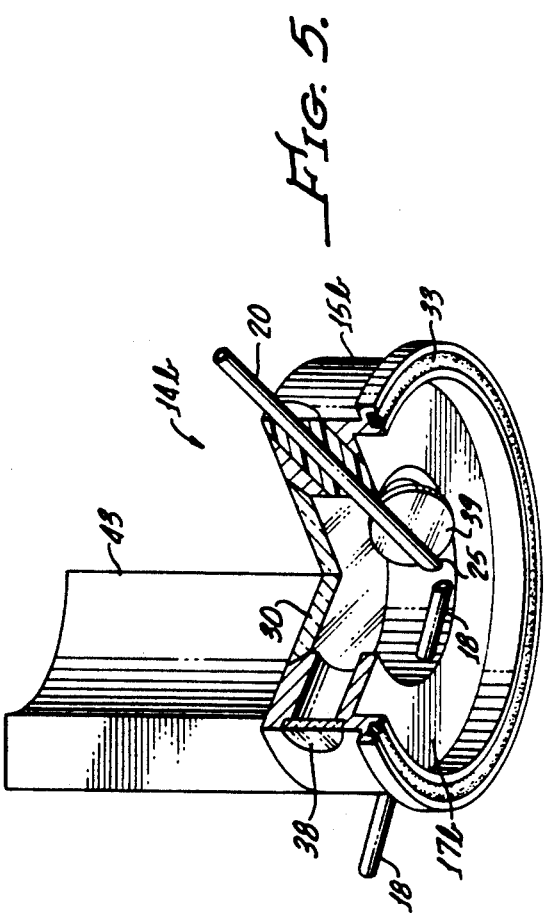
FIG. 5 shows a perspective cut-away view of the sample chamber shown in FIG. 3.

FIG. 5 is a sectioned perspective view of the chamber 14b shown in FIGS. 3 and 4. The attachment member 43 can be strapped to the microscope lens barrel. The strapped position again obtains a common focal plane/spot when the end seal 33 abuts the glass slide 35a (see FIG. 3) to seal cavity 17b from the bottom. Protruding into cavity 17b are sections of inert gas piping 18 and collection piping 20. The collection piping 20 is thermally insulated from container 15b. A laser window 38 covers another aperture in the walls of container 15b, which is aligned so that the laser beams (see FIG. 3) reflected from laser mirror 39 onto a plane parallel to the exposed surface of the sample (see FIG. 3). Window 30 covers still another container 15b aperture at the top near the microscope.

Figure 6:
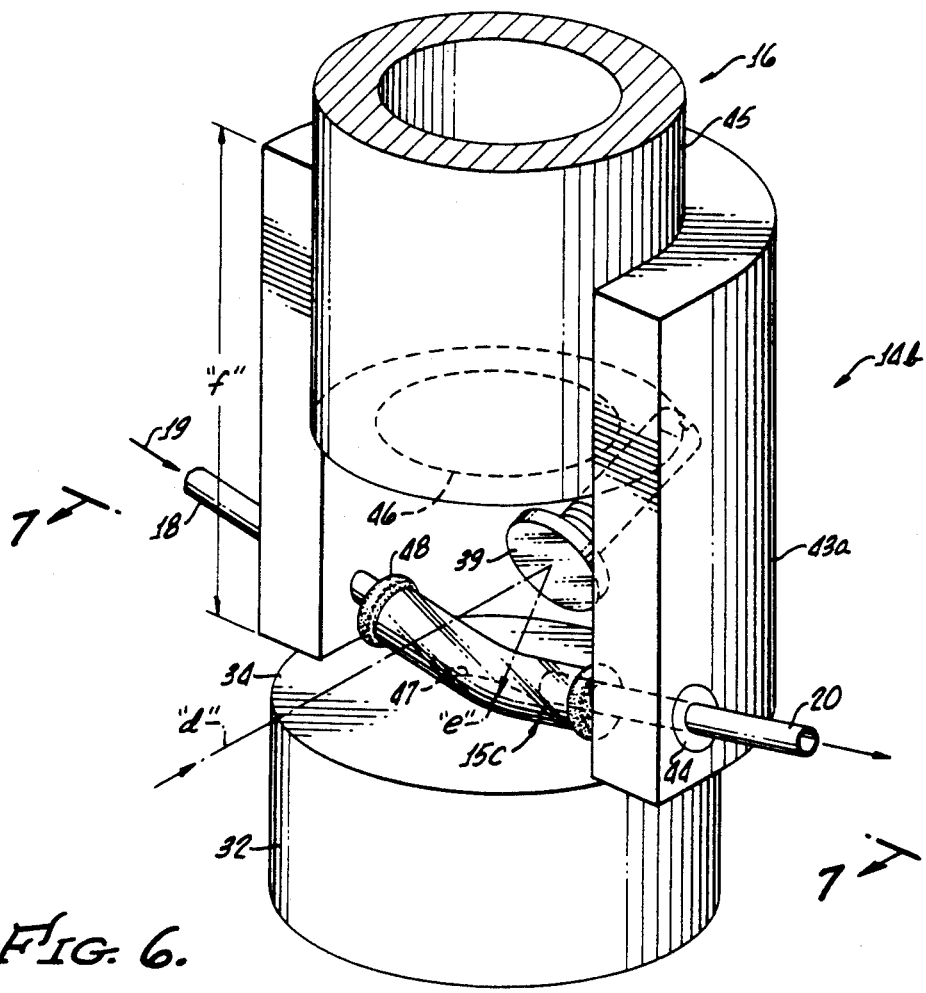
FIG. 6 shows a perspective side view of the preferred embodiment of the sample chamber portion of the apparatus.

FIG. 6 is a perspective view of the preferred embodiment of the sample chamber portion of the apparatus. The objective lens barrel 45 of the microscope 16 is attached to an attach member 43a. Attachment supports a tubular or duct-like container 15c in a position just above the focal plane (and coincident with the exposed sample surface 34) of the microscope. This position is also coincident with focal spot "e" at the end of the converging laser beam "d". Alternative embodiments may strap the attach member 43a to the lens barrel of the microscope. The lens barrel 45 of microscope 16 holds an objective lens 46 proximate to the sample surface 34 at a distance "b" (see FIG. 2).

The tubular chamber 15c has a lower aperture 47 shaped and dimensioned to partially abut the contact sample surface 34 when the chamber 14c is lowered or sample surface 34 raised. The abutted position is not designed to create an absolutely fluid tight seal of the cavity 17c. The position need only to restrict and minimize the loss at the abutted interface of inert gas flow (shown as an inflow arrow) from inert gas piping 18 when compared to the amount of inert gas flow recovered (shown as outflow arrow) in collection piping 20. A small relative loss of pyrolyzate (and inert) gas at the abutted interface does not significantly impair the analysis of the pyrolyzate gas.

The ceramic insulation 44 again insulates and supports the collection piping portion protruding (shown dotted) into the tubular chamber 15c. Protruding portion extends to nearby the sealing or contacting aperture 47, proximate to the particle of interest on the sample surface 34 of sample 32. The insulated collection piping can be either conductively heated (to prevent gas condensation) or cooled (to trap pyrolyzate gases while allowing the inert gases to pass through).

The tubular shape of the container 15c further assists in the sweeping and collection of pyrolyzate gases. The tubular chamber is composed of quartz or other material transparent to optical and near-infrared frequency radiations. The tubular shape also presents a nearly perpendicular surface to vertical (visible) radiations to the lens barrel of the microscope 16 and reflected near-infrared laser beam "d" from laser mirror 39. The entire quartz tubular container 15c may also be heated (or cooled) and the aperture sealed with an elastomeric O-ring if reductions in the loss of pyrolyzate gases are required.

A silicone plug 48 joins the end of tubular container 15c and supply piping systems 18. Alternative embodiments can also extend the gas supply piping 18 into the tubular chamber 15c similar to the prior alternative embodiments. In addition, the portion of the collection piping 20 protruding into the tubular chamber 15c can be deleted if the container's tubular shape, heating or cooling, or aperture sealing collects a sufficient fraction of the pyrolyzates generated by the laser beam "d".

The height "f" of attachment member 43a provides a set-off distance from the objective lens 46 to the sample surface 34. This set-off distance places the sample surface 34 proximate to aperture 47 in the focal plane of the microscope lenses and coincident with the focal spot "e" when the aperture is in contact with sample surface 34.

Figure 7:
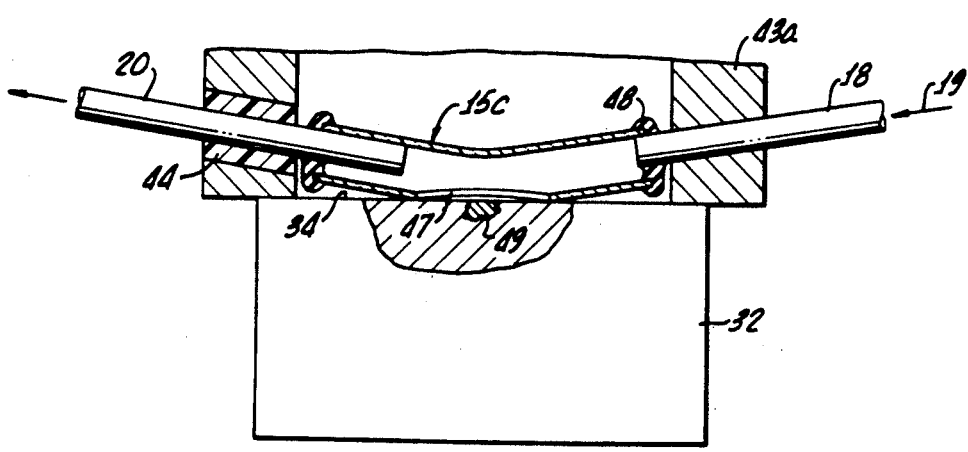
FIG. 7 shows a cross sectional view of the preferred embodiment sample chamber.

FIG. 7 is a cross sectional view 7—7 as shown on FIG. 6 of the preferred tubular chamber. Laterally moving the particle of interest 49 can place it directly under the aperture 47 of the tubular chamber 15c. The tubular chamber is slightly bent near the aperture 47 to direct (sweep) inert gas flow (inflow arrow) from gas supply piping system 18 across the aperture 47 and the particle of interest 49. The shape of tubular container and collection piping 20 collects swept inert and pyrolyzate gases into the trap (see FIG. 1). The aperture is shaped to contact the exposed surface 34 of the sample 32. The aperture 47 is also shaped and dimensioned to place the particle of interest within the focal plane/spot of the microscope and laser systems (see FIG. 1). Alternative embodiments can include straight duct-like chambers or non-circular cross-sectional duct dimensions.

The operational process of using the preferred embodiment of the analyzer chamber shown in FIGS. 6 and 7 first encases and polishes the sample surface containing the particle(s) of interest. The composite sample is attached by compressing putty against a glass slide using a stop fixture and a pressing tool to orient and position the polished surface. Raising the attached sample (i.e., raising the microscope stage) abuts the sample surface against the contact surface (opening or aperture edges 49) of the tubular chamber 15c. The polished surface 34 forms a low gas loss interface to generally enclose any pyrolyzate effluents within the tubular chamber 15c.

The height of the abutting surface of the chamber 15c acts as a measured set-off distance spacer, putting the sample surface into the optical focal plane of maximum optical detection sensitivity. The operator then scans the sample surface 34 within the microscope's field of view and selects a spot as small as 10 microns on the particle of interest 49. The visible laser beam (see FIG. 1) and a laser mirror are adjusted to place the visible laser beam onto the selected spot.

The chamber is purged, and the near infrared laser duration and intensity controls selected. The selected duration and intensity of the laser beam must expose the particle to sufficient absorbed energy to generate a gaseous pyrolyzate from the 10 micron spot on the particle. The depth of pyrolysis of the sample is a function of laser beam intensity and duration, as well as the absorption characteristics of the particle. After and during laser heating, the generated pyrolyzate gases are sucked along with an inert gas to a cold trap, which passes the inert carrier gas but condenses the pyrolyzate gases.

Sufficient pyrolyzate quantities are collected in the cold trap by repeating the procedure at different spots (or to a different depth). The quantity collected is sufficient for analysis by a gas chromatograph and mass spectrometer. When analysis is desired, the coolant supply to the cold trap is removed. Increasing the gas chromatograph oven temperature moves the pyrolyzate gases through the gas chromatograph's capillary column at a rate dependent upon their molecular weight and vapor pressure. The optical information and analysis of the pyrolyzate compounds determine the composition and properties of the particle of interest.

The advantages of this device and method include: an ability to optically and thermally analyze an entire or portion(s) of a single small microscopic-sized particle or type of small particle; the flexibility to analyze or store multiple quantities of pyrolyzate from a particle; accomplishing the focus and enclosing of the sample in a single step; the prevention of pyrolyzate gas loss by the chamber shape and conduction heating of the protruding collection tube; and avoiding design compromises of the prior microscope and laser systems.

Still other alternative embodiments of the invention are possible. These include: incorporating the microscope lens as part of the chamber enclosure (i.e., extending the chamber to seal against the lens or lens barrel of the microscope); providing an unattached or non-encased sample (i.e., a sample placed, but not attached to a glass slide); providing the duct-like tube within a second chamber such as placing the duct-like chamber 15c shown in FIG. 7 within the chamber 15a shown in FIG. 2, (to further sweep and direct gas flows); colinearly transmit the microscope's field of view and laser beams through a single window; and replacing the abutting chamber end contact surface with an aperture having a circumferential edge contact surface with the sample (i.e., the aperture shaped to act as a sliding ring seal or closely spaced apart surface around the edge diameter of the sample), allowing further focal adjustment without loss of a sealed chamber or a high loss of fluid.

While the preferred embodiment of the invention has been shown and described, and some alternative embodiments also shown and/or described, changes and modifications may be made thereto without departing from the invention. Accordingly, it is intended to embrace within the invention all such changes, modifications and alternative embodiments as fall within the spirit and scope of the appended claims.

What is claimed is:

1. An apparatus for analyzing a particle within a sample, said apparatus comprising:

a sensor capable of detecting emitted radiation from said particle within a detection zone, said sensor detecting emitted radiation centered around an axis and said zone located substantially around a portion of said axis wherein detection sensitivity of said sensor is substantially at a maximum sensitivity from within said zone;

a chamber attached to said sensor wherein at least a portion of said chamber extends along said axis towards said particle, said chamber having a first chamber aperture located substantially around said axis;

a contact surface for setting said particle, at least a portion of said contact surface spaced apart from said particle, said contact surface shaped and dimensioned to contact a portion of said chamber located near said first aperture when said particle is within said zone, wherein said contact surface and the set particle can be spaced apart from said chamber;

means for changing the relative spacing between said set particle and said chamber, so that when said contact surface is substantially contacting said chamber, a partial boundary is formed around said particle by said chamber and said contact surface;

means for transmitting said emitted radiation from the partially bounded particle to said sensor;

a source of energy capable of heating said particle until a fluid emanates from a portion of the partially bounded particle;

means for transferring energy from said energy source to a portion of the partially bounded particle;

means for collecting said fluid from said chamber.

2. The apparatus of claim 1 wherein said chamber also comprises an abutting end surface at or near said first aperture.

3. The apparatus of claim 2 wherein said radiation is visible light and said sensor is a microscope having an objective lens.

4. The apparatus of claim 3 wherein said chamber also comprises a first window located substantially around said axis and attached to a second aperture, wherein said first window is transparent to radiation within the visible frequency band and said window is located at or near said objective lens.

5. The apparatus of claim 4 wherein said contact surface is a generally planar surface perpendicular to said axis, wherein said contact surface is movably mounted to said microscope, said contact surface capable of moving in a directions perpendicular and parallel to said axis.

6. An apparatus for analyzing a particle within a sample, said apparatus comprising:

a sensor capable of detecting emitted radiation from said particle within a detection zone, said sensor detecting emitted radiation centered around an axis and said zone located substantially around a portion of said axis wherein detection sensitivity of said sensor is substantially at a maximum sensitivity from within said zone;

a chamber attached to said sensor wherein at least a portion of said chamber extends along said axis towards said particle, said chamber having a first chamber aperture located substantially around said axis;

a contact surface for setting said particle, at least a portion of said contact surface spaced apart from said particle, said contact surface shaped and dimensioned to contact a portion of said chamber located near said first aperture when said particle is within said zone, wherein said contact surface and the set particle can be spaced apart from said chamber;

means for changing the relative spacing between said set particle and said chamber, so that when said contact surface is substantially contacting said chamber, a partial boundary is formed around said particle by said chamber and said contact surface;

means for transmitting said emitted radiation from the partially bounded particle to said sensor;

a source of energy capable of heating said particle until a fluid emanates from a portion of the partially bounded particle;

means for transferring energy from said energy source to a portion of the partially bounded particle;

means for collecting said fluid from said chamber;

wherein said chamber also comprises an abutting end surface at or near said first aperture;

wherein said radiation is visible light and said sensor is a microscope having an objective lens;

wherein said chamber also comprises a first window located substantially around said axis and attached to a second aperture, wherein said first window is transparent to radiation within the visible frequency band and said window is located at or near said objective lens;

wherein said contact surface is a generally planar surface perpendicular to said axis, wherein said contact surface is movably mounted to said microscope, said contact surface capable of moving in a directions perpendicular and parallel to said axis; and wherein said source of energy comprises a controlled intensity and duration laser beam source of a heating beam along a path from said energy source to said particle wherein a portion of said path diverts from said axis, said energy source capable of generating a fluid pyrolyzate from said particle; and wherein said means for transferring energy comprises:

a second chamber window attached to a third aperture of said chamber which is separated from said first window, said second chamber window located along the path of said heating beam and wherein said second window is generally translucent to said heating beam; and means for directing said heating beam onto a portion of said particle.

7. The apparatus of claim 6 wherein said second window is spaced apart from said first window.

8. The apparatus of claim 6 wherein said source of energy produces a near-infrared frequency heating laser beam directed towards said second chamber window and said means for transferring energy also comprises:

a digitally controlled shutter controlled by a controller and located along the path of said heating laser beam, the shutter limiting the passage of said heating beam when closed; and wherein said means for directing comprises at least one mirror adjustably mounted within said chamber.

9. The apparatus of claim 8 wherein said chamber has a threadable attachment surface and said mirror is threadably attached to said chamber.

10. The apparatus of claim 9 which also comprises:

means for chemically analyzing said collected pyrolyzate fluid outside said chamber; and means for transporting said collected pyrolyzate fluid to said means for chemically analyzing.

11. The apparatus of claim 10 wherein said means for chemically analyzing comprises a chromatographic analyzer device and a spectrometer analyzer device, and said means for transporting comprises a heated duct attached to said chamber.

12. The apparatus of claim 11 wherein said means for chemically analyzing is connected to said means for transporting and said means for chemically analyzing also comprises a means for selectably controlling the transfer of said pyrolyzate fluid to said analyzer devices.

13. The apparatus of claim 12 wherein said means for selectably controlling comprises a 6-way valve.

14. The apparatus of claim 13 which also comprises:
   means for evacuating the interior of said chamber attached to an aperture of said chamber;
   means for supplying inert gas to said interior attached to an aperture of said chamber for purging the interior of said chamber with inert gas; and
   a source of inert gas connected to said means for supplying.

15. The apparatus of claim 14 which also comprises a targeting laser source capable of producing a visible laser beam colinear with said heating laser beam within said chamber.

16. The apparatus of claim 15 wherein said laser sources also include a means for focusing said laser beams onto an area on a planar surface of said sample, a portion of which is substantially within said chamber, said area having a representative dimension as small as 10 microns in diameter.

17. The apparatus of claim 15 wherein said contact surface is a glass slide.

18. The apparatus of claim 17 wherein said sample is attached to said glass slide by means of a putty-like material.

19. The apparatus of claim 18 wherein said sample is cast in an encasing material which fully encloses said sample except for an exposed surface, and said putty-like material is attached to a surface of said encasing material distal from said exposed surface.

20. The apparatus of claim 19 wherein said encasing material is a clear acrylic plastic.

21. The apparatus of claim 15 wherein said at least a portion of said contact surface not including said particle comprises a polished surface of said sample.

22. An apparatus for use when analyzing a small particle within a sample, said apparatus comprising:
   an optical sensor having a focal plane, said sensor sensing said small particles when located in a zone which includes said focal plane;
   a source of heat capable of heating said particle and generating a fluid pyrolyzate from said particle when it is located substantially in said focal plane;
   a walled chamber only partially enclosing a cavity, said chamber having an aperture in a first wall section, and a second wall section located proximate to said optical sensor;
   a relatively planar sealing surface for sealing said aperture wherein said planar sealing surface is attachable to said particle;
   means for concurrently moving said sample and said planar sealing surface to a position relative to said chamber, said position substantially intersecting said axis and parallel to said focal plane when said sealing surface is sealably abutting said aperture, wherein said abutted chamber and said sealing surface form unattached segments of an enclosed cavity;
   means for transmitting heat from said heat source to a portion of said particle, wherein said means for transmitting heat is separate from said means for transmitting light; and
   means for collecting said fluid pyrolyzate.

23. An apparatus for use when analyzing a small particle within a composite sample having a sealing surface, said apparatus comprising:
   an optical sensor having a focal plane, said sensor sensing said small particle when located within a zone which includes said focal plane;
   a source of heat capable of heating said particle and generating a fluid pyrolyzate from said particle when it is located within said zone;
   a walled chamber partially enclosing a cavity, said chamber having an apertured first wall section, and a second wall section located proximate to said optical sensor;
   means for locating said sealing surface and said sample within said zone when said apertured wall section is abutting said sealing surface, wherein said abutted chamber and said sealing surface form unattached segments of a cavity generally enclosing said particle;
   means for transmitting light from said sealing surface to said optical sensor; and
   means for transmitting heat from said heat source to said particle.

24. An apparatus for use when analyzing a small particle within a composite sample, said apparatus comprising:
   an optical sensor having a focal plane, said sensor sensing said small particle when located within a zone which includes said focal plane;
   a source of heat capable of heating said particle and generating a fluid pyrolyzate from said particle when said particle is located within said zone;
   a walled chamber partially enclosing a cavity, said chamber having an apertured first wall section, and a second wall section located proximate to said optical sensor;
   a chamber sealing surface detachably connected to said sample, said sealing surface located within a first specific distance from said focal plane and within a second specific distance from one of the surfaces of said sample;
   means for transmitting light from said cavity to said optical sensor;
   means for sealably abutting said apertured first wall section to said sealing surface, wherein said abutted chamber and said sealing surface form unattached segments of an enclosed cavity wherein the abutting motion changes the relative spacing between the sealing surface and particle;
   means for transmitting heat from said heat source to a portion of said particle, wherein said means for transmitting energy is separate from said means for transmitting light; and
   means for collecting said fluid pyrolyzate.

25. A chamber apparatus for analyzing a particle within a composite sample, said apparatus comprising:
   a walled chamber capable of partially enclosing said particle;
   a source of heat capable of generating a fluid pyrolyzate from said particle when partially enclosed by said chamber;
   an analyzer capable of detecting a property of said fluid pyrolyzate;
   a duct for passing said fluid pyrolyzate passing through an aperture of said partial enclosure, a first portion of said duct having a first end generally outside said partial enclosure, and a second end of said first portion connected to said analyzer;
   means for heating said first duct portion, wherein said means for heating is capable of maintaining said first duct portion above a first minimum temperature;

a second duct portion attached at one end to said first end of said first duct portion, said second duct portion transporting said fluid pyrolyzates from near said enclosed particle to said first end of said first portion, wherein a said second duct portion is composed of a thermally conductive material in thermal contact with said means for heating;

means for thermally insulating said duct from said sample; wherein said thermal insulating and heating means are capable of maintaining said second duct portion above a second minimum temperature sufficient to prevent a change of phase of said fluid pyrolyzate within said second duct portion when said first duct portion is at said first minimum temperature; and means for transporting said fluid within said duct.

26. The apparatus of claim 25 wherein said means for transporting comprises:

a source of inert gas;

a third duct portion connecting said inert gas source to said chamber; and means for moving said inert gas and said pyrolyzate fluid.

27. The apparatus of claim 26 wherein said third duct portion is partially composed of an aluminum containing material.

28. The apparatus of claim 26 wherein said heating and thermal insulating means are also capable of maintaining the temperature of said chamber below a third temperature, when said chamber is cooled by natural convention contact with ambient air.

29. The apparatus of claim 28 wherein the shape of said second duct portion is capable of being deformed into a plurality of positions, wherein at least one of said positions is capable of transporting a portion of said pyrolyzate fluid to said analyzer when carried along with said inert gas.

30. The apparatus of claim 29 wherein said second duct portion is partially composed of a copper containing material.

31. The apparatus of claim 29 wherein said duct is partially composed of brass.

32. The apparatus of claim 31 wherein said duct is composed of exterior brass tube sections in concentric thermal contact with interior tubes sections composed of a nickel containing material.

33. The apparatus of claim 32 wherein said thermal insulating means comprises a ceramic insulator material attached to one of said wall sections and said insulating means is also capable of supporting one of said tubes.

34. The apparatus of claim 33 wherein said ceramic insulating means is capable of maintaining said second duct portion at said second minimum temperature when the fluid and inert gas pressure within said chamber is approximately one atmosphere.

35. The apparatus of claim 34 wherein said source of heat is a directable laser beam capable of impingement upon a portion of said enclosed particle.

36. The apparatus of claim 35 which also comprises a translucent window attached to one of said walls in the path of said laser beam, said window capable of transmitting said laser beam to the interior of said chamber.

37. A chamber apparatus for analyzing one type of particle within a composite sample having a plurality of particles of said one particle type, said apparatus comprising:

first means for generating a first quantity of a fluid pyrolyzate from a first portion of one of said plurality of particles of said one particle type;

second means for generating a second quantity of said fluid pyrolyzate from a second portion of one of said plurality of particles of said one particle type;

a walled chamber capable of partially containing each of said fluid pyrolyzate quantities;

means for collecting each of said fluid pyrolyzate quantities from said chamber to outside said chamber;

means for trapping said collected quantities of pyrolyzate outside said chamber;

a pyrolysis fluid analyzer connected to said means for trapping, wherein said analyzer requires a minimum resolution amount of fluid;

means for releasing trapped quantities of pyrolyzate in an amount at least equal to said minimum resolution amount; and means for transporting said released quantities to said analyzer.

38. The apparatus of claim 37 which also comprises means for supplying said chamber with an inert gas.

39. The apparatus of claim 38 which comprises a plurality of said pyrolysis fluid analysis sensors within said pyrolysis fluid analyzer to analyze the different quantities of pyrolysis fluids.

40. The apparatus of claim 39 wherein said means for generating comprises a laser beam energy source generating a laser beam having a frequency which is partially absorbed by said particle portions and wherein said absorbed energy is converted into heat.

41. The apparatus of claim 40 wherein the first of said sensors comprises a gas chromatograph device and a second of said sensors comprises a mass spectrometer, wherein a pyrolyzate fluid output of said gas chromatograph is connected to an input of said mass spectrometer device.

42. A chamber apparatus for analyzing one type of particle within a composite sample having a plurality of particles of said one particle type, said apparatus comprising:

first means for generating a first quantity of a fluid pyrolyzate from a first portion of one of said plurality of particles of said one particle type;

second means for generating a second quantity of said fluid pyrolyzate from a second portion of one of said plurality of particles of said one particle type;

a walled chamber capable of partially containing each of said fluid pyrolyzate quantities;

means for collecting each of said fluid pyrolyzate quantities from said chamber to outside said chamber;

means for trapping said collected quantities of pyrolyzate outside said chamber;

a pyrolysis fluid analyzer connected to said means for trapping, wherein said analyzer requires a minimum resolution amount of fluid;

means for releasing trapped quantities of pyrolyzate in an amount of at least equal to said minimum resolution amount;

means for transporting said released quantities to said analyzer;

means for supplying said chamber with an inert gas;

a plurality of said pyrolysis fluid analysis sensors in said pyrolysis fluid analyzer to analyze the different quantities of pyrolysis fluids;

wherein said means for generating comprises a laser beam energy source generating a laser beam having a frequency which is partially absorbed by said particle portions and wherein said absorbed energy is converted into heat;

wherein the first of said sensors comprises a gas chromatograph device and a second of said sensors comprises a mass spectrometer, wherein a pyrolyzate fluid output of said gas chromatograph is connected to an input of said mass spectrometer device; and wherein said means for trapping comprises a cold trap cooled by a source of liquid nitrogen coolant, wherein said cold trap is capable of condensing gaseous pyrolyzates.

43. The apparatus of claim 42 wherein said means for releasing comprises:

means for controlling said coolant supplied to said cold trap; and means for heating said cold trap to a temperature capable of vaporizing a portion of said condensed pyrolyzates.

44. The apparatus of claim 43 wherein said means for generating procedures at least one of the fluid pyrolyzate quantities smaller than said minimum resolution amount.

45. An apparatus for analyzing a particle within a composite sample comprising:

a laser beam source generating a controlled duration heating laser beam having a representative initial beam cross sectional dimension at a first location, said beam capable of impinging on one surface of said sample and generating a fluid pyrolyzate;

a walled chamber capable of partially containing said fluid pyrolyzate;

a fluid pyrolyzate analysis sensor in fluid communication with said chamber;

means for enlarging said initial heating beam dimension located between said first location and said particle;

means for converging said enlarged heating beam dimension to produce a focal spot located at or near a portion of said particle and having a representative cross sectional spot dimension smaller than said initial heating beam dimension; and means for transporting said generated pyrolyzate from said walled chamber to said sensor.

46. The apparatus of claim 45 which also comprises:

a targeting laser beam source for targeting said heating beam, said targeting laser beam capable of generating a visible beam within said chamber colinear with said heating beam; and means for adjustably directing said visible beam and said converging heating onto said particle.

47. The apparatus of claim 46 wherein said means for adjustably directing is a multi-position mirror attached to said chamber.

48. The apparatus of claim 47 wherein said initial beam dimension is a diameter no larger than 2 mm. and said means for converging is an achromatic generally circularly shaped lens having a diameter of at least 1.5 cm.

49. An apparatus for analyzing a particle within a sample having a plurality of particles, said apparatus comprising:

a remote sensor capable of detecting radiation emitted from said particle, said sensor having an axis around which detected radiation is centered and having a zonal distance along a portion of said axis wherein detection sensitivity of said sensor is nearly maximum;

a walled chamber attached to said sensor and partially enclosing a cavity, said chamber having a first aperture in a first wall section located distal from said sensor and at or near said axis;

a first aperture sealing surface attached to said particle, said sealing surface shaped and dimensioned to mate with said first aperture when said connected particle is at or near said axis and within said zonal distance;

a means for moving said first aperture sealing surface in a direction having a component generally parallel to said axis; wherein said moving means is capable of sealably abutting said first aperture to said sealing surface to form a generally enclosed cavity;

a laser beam heat source producing a heating beam of controlled duration and having a representative initial beam cross sectional dimension, said beam capable of generating a plurality of fluid quantities from said particle when within said enclosed cavity;

a targeting laser beam source generating a visible beam colinear with said heating beam within said chamber;

means for enlarging said initial heating beam dimension;

means for converging said enlarged heating beam dimension, wherein said means for converging is capable of producing a focal spot within said chamber having a representative cross sectional spot dimension smaller than said beam cross sectional dimension and said focal spot is located at or near said zonal distance when said particle is enclosed;

a beam window attached to a wall section of said chamber, and located in the path of said converging heating beam when said particle is enclosed;

means for adjustably directing said visible beam and said focal spot onto said particle;

a first chromatographic analyzer of said fluid;

a second mass spectroscopic analyzer of said fluid;

a duct for transporting said fluid to said analyzers, said duct comprising a first portion duct having a first end at or near one of said wall sections and a second end in fluid communication with said analyzers;

means for heating said first duct, wherein said means for heating is capable of maintaining said first duct portion above a first minimum temperature;

a second duct portion for transporting said fluid from near said particle within said chamber to said first end of said first duct portion, wherein said second duct portion is partially composed of a thermally conductive material and is in thermal contact with said first duct means;

means for supporting and thermally insulating said ducts from said walled chamber; wherein said insulating means is capable of maintaining said second duct above a second minimum temperature sufficient to prevent a change of phase of said fluid within said second duct when transporting said fluid and when said first duct is at said first temperature; means for trapping said generated quantities of gaseous fluid; and means for releasing said trapped quantities of gaseous fluid to said analyzers, wherein said released amount is at least equal to said minimum resolution amount.

50. The apparatus of claim 49 wherein:
said remote sensor is a microscope and said detected radiation is visible light;
said means for moving comprises a microscope stage translating mechanism;
said laser beam source produces a laser beam within the near-infrared, middle-infrared and far-infrared frequency ranges;
said means for enlarging and said means for converging said heating beam comprise lenses placed in the path of said laser beam;
said means for adjustable directing comprises a mirror threadably attached to said chamber;
said means for supporting and thermally insulating comprising a ceramic insulator material connecting said chamber and one of said ducts;
said means for trapping comprises a cold trap and a source of coolant; and
said means for releasing comprises a control valved connection of said coolant to said cold trap, and means for heating said cold trap.

51. A chamber apparatus for analyzing a particle within a composite sample, said apparatus comprising:
a chamber for at least partially enclosing said sample;
means for moving of said sample to contact a portion of said chamber, at least a portion of said sample located within said chamber when in contact;
a source of heat capable of generating a fluid pyrolyzate from said particle when said sample is in contact with said chamber, wherein said chamber is capable of partially enclosing said fluid pyrolyzate;
an analyzer capable of detecting a property of said fluid pyrolyzate when said fluid pyrolyzate is transported to said analyzer;
a thermally conductive duct for transporting said fluid pyrolyzate from said camber to said analyzer, wherein said duct is comprised of a first duct portion having a first end outside said partial enclosure, and a second end in fluid communication with said analyzer;
means for reducing the temperature of said first duct portion until said first duct portion is below a first maximum temperature;
a second duct portion for trapping said partially enclosed fluid pyrolyzate, said second duct portion extending from near said particle to said first end of said first duct portion; and
means for thermally insulating said duct from said sample; wherein said thermal insulating and said reducing means are capable of maintaining said second duct portion below a second maximum temperature sufficient to change the phase of said fluid pyrolyzate within said second duct portion when said first duct portion is at said first maximum temperature.

52. An apparatus for analyzing a particle within a sample, said apparatus comprising:
a sensor capable of detecting radiation issuing from said particle, said sensor detecting radiation centered around an axis and having a focal zone located so that it includes a focal distance along a portion of said axis wherein detection sensitivity of said sensor within said focal zone is substantially at a maximum;
a source of a heating laser beam capable of heating and generating a fluid from a portion of said particle;
a chamber extended along a portion of said axis and partially enclosing a cavity and attached to said sensor, said chamber comprising:
a fluid impermeable wall composed of materials transparent to said issued radiation and said heating laser beam;
a touch surface attached to said chamber for contacting a contact surface; and
a first chamber aperture near said touch surface, located in said wall substantially around said axis;
a contact member for more fully enclosing said chamber and spaced apart from said particle, said contact member having a contact surface shaped and dimensioned to contact said touch surface when said spaced apart particle is at or near said focal zone;
a means for concurrently moving said contact member and said spaced apart particle towards said touch surface until said contact member reaches said contact surface forming a partial boundary around said fluid generated by said heating laser beam; and
means for collecting said fluid from said chamber.

53. The apparatus of claim 52 wherein said chamber is a duct-like shape having a first duct end and a second duct end connected to said means for collecting, wherein said first chamber aperture is located nearly equidistant from said first and second duct ends.

54. The apparatus of claim 53 which also comprises:
means for supplying inert gas to said first duct end; and
a source of inert gas connected to said means for supplying.

55. The apparatus of claim 54 said duct-like chamber is shaped and dimensioned to sweep said inert gas across said first chamber aperture to said means for collecting.

56. The apparatus of claim 55 wherein said duct-like chamber is tubular having a fluid flow deviation form located at or near said first chamber aperture.

57. The apparatus of claim 55 wherein said chamber is composed of clear quartz.

58. The apparatus of claim 57 wherein said means for collecting is a tube thermally insulated from and attached to said chamber.

59. The apparatus of claim 55 wherein said touch comprises an abutting portion of said duct-like chamber, wherein said abutting portion is shaped and dimensioned to form a generally gas tight seal.

60. An apparatus for analyzing a particle within a sample having a plurality of particles, said apparatus comprising:
a remote sensor capable of detecting radiation emitted from said particle, said sensor having an axis around which detected radiation is centered and having a zone along a portion of said axis wherein detection sensitivity of said sensor is nearly maximum;
a walled chamber attached to said sensor and partially enclosing a cavity extending along said axis and having an aperture in a wall section located distal from said sensor;
a support member for supporting said particle at a distance from said sensor, said support member having an aperture sealing surface shaped and dimensioned to mate with said aperture when said particle is supported within said zone, wherein said mated support member and chamber forms a substantially enclosed cavity around said particle;

a means for changing said distance wherein said changing means concurrently changes the distance between said aperture and said sealing surface.

61. The apparatus of claim 60 which also comprises:

a laser beam heat source producing a heating beam capable of being transmitted into said cavity and generating a fluid quantity from said particle within said enclosed cavity; and means for chemically analyzing said fluid quantity.

62. An apparatus for analyzing a particle within a sample, said apparatus comprising:

a sensor capable of detecting emitted radiation from said particle within a detection zone, said sensor detecting emitted radiation centered around an axis and said zone located substantially around a portion of said axis wherein detection sensitivity of said sensor is substantially at a maximum sensitivity from within said zone;

a chamber attached to said sensor wherein at least a portion of said chamber extends along said axis towards said particle, said chamber having a first chamber aperture located substantially around said axis;

a contact surface for setting said particle, at least a portion of said contact surface spaced apart from said particle, said contact surface shaped and dimensioned to seal the first aperture of said chamber when said particle is within said zone, wherein said contact surface and the set particle can be spaced apart from said chamber;

means for changing the relative spacing between said set particle and said chamber so that when said contact surface is substantially contacting said chamber, a partial boundary is formed around said particle by said chamber and said contact surface.

63. The apparatus of claim 62 which also comprises:

means for transmitting said emitted radiation from the partially bounded particle to said sensor;

a source of energy capable of heating said particle until a fluid emanates from a portion of the partially bounded particle;

means for transferring energy from said energy source to a portion of the partially bounded particle; and wherein said source of energy comprises a controlled intensity and duration laser beam source of a heating beam along a path from said energy source to said particle, said energy source capable of generating a fluid pyrolyzate from said particle.

* * * * *

UNITED STATES PATENT AND TRADEMARK OFFICE
CERTIFICATE OF CORRECTION

PATENT NO. : 5,147,611
DATED : September 15, 1992
INVENTOR(S) : Stout et al.

It is certified that error appears in the above-identified patent and that said Letters Patent is hereby corrected as shown below:

Claim 51, column 23, line 40, "camber" should be changed to -- chamber --.

Signed and Sealed this

Seventh Day of September, 1993

Attest:

BRUCE LEHMAN

Attesting Officer

Commissioner of Patents and Trademarks